US006379690B2

United States Patent
Blanchard et al.

(10) Patent No.: US 6,379,690 B2
(45) Date of Patent: *Apr. 30, 2002

(54) KERATIN-BASED HYDROGEL FOR BIOMEDICAL APPLICATIONS AND METHOD OF PRODUCTION

(75) Inventors: Cheryl R. Blanchard, Warsaw, IN (US); Scott F. Timmons, San Antonio, TX (US); Robert A. Smith, Jackson, MS (US)

(73) Assignee: Keraplast Technologies, Ltd., Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/736,957

(22) Filed: Dec. 12, 2000

Related U.S. Application Data

(63) Continuation of application No. 09/365,699, filed on Aug. 2, 1999, now Pat. No. 6,159,496, which is a continuation of application No. 08/979,456, filed on Nov. 26, 1997, now Pat. No. 5,932,552.

(51) Int. Cl.$^7$ .............. A61F 13/00; A61F 2/00; A61F 15/00; A61F 38/00; A61F 38/12

(52) U.S. Cl. ............ 424/422; 424/400; 424/423; 424/445; 514/21; 514/944; 530/357; 530/842

(58) Field of Search .............. 424/400, 422, 424/423, 445; 514/21, 944; 530/357, 842

(56) References Cited

U.S. PATENT DOCUMENTS

| | | | |
|---|---|---|---|
| 3,867,728 A | 2/1975 | Stubstad et al. ............ 3/1 |
| 3,875,595 A | 4/1975 | Froning .................. 3/1 |
| 3,987,497 A | 10/1976 | Stoy et al. .............. 3/1 |
| 4,021,382 A | 5/1977 | Stoy et al. ........ 260/2.5 M |
| 4,026,296 A | 5/1977 | Stoy et al. ........ 128/349 B |
| 4,060,081 A | 11/1977 | Yannas et al. ......... 128/156 |
| 4,107,121 A | 8/1978 | Stoy ............... 260/29.6 AB |
| 4,123,406 A | 10/1978 | Stoy et al. ....... 260/29.6 AN |
| 4,172,823 A | 10/1979 | Stoy et al. ....... 260/29.6 AN |
| 4,183,884 A | 1/1980 | Wichterle et al. ......... 264/41 |
| 4,228,056 A | 10/1980 | Stoy ............... 260/29.6 AN |
| 4,309,777 A | 1/1982 | Patil ...................... 3/1.91 |
| 4,349,921 A | 9/1982 | Kuntz ....................... 3/1 |
| 4,357,274 A | 11/1982 | Werner ............... 260/123.7 |
| 4,485,097 A | 11/1984 | Bell ........................ 424/95 |
| 4,570,629 A | 2/1986 | Widra ................... 128/156 |
| 4,685,447 A | 8/1987 | Iversen et al. ......... 128/1 R |
| 4,714,469 A | 12/1987 | Kenna ..................... 623/17 |
| 4,772,287 A | 9/1988 | Ray et al. ................. 623/17 |
| 4,904,260 A | 2/1990 | Ray et al. ................. 623/17 |
| 4,904,261 A | 2/1990 | Dove et al. ............... 623/17 |
| 4,911,718 A | 3/1990 | Lee et al. ................. 623/17 |
| 4,932,969 A | 6/1990 | Frey et al. ................ 623/17 |
| 4,936,848 A | 6/1990 | Bagby .................... 623/17 |
| 4,946,378 A | 8/1990 | Hirayama et al. ......... 623/17 |
| 4,959,213 A | 9/1990 | Brod et al. ................ 514/21 |
| 4,969,888 A | 11/1990 | Scholten et al. .......... 606/94 |
| 5,035,716 A | 7/1991 | Downey ................. 623/17 |
| 5,047,055 A | 9/1991 | Bao et al. ............... 623/17 |
| 5,047,249 A | 9/1991 | Rothman et al. ........ 424/543 |
| 5,059,193 A | 10/1991 | Kuslich .................. 606/61 |
| 5,123,926 A | 6/1992 | Pisharodi ............... 623/17 |
| 5,192,326 A | 3/1993 | Bao et al. ............... 623/17 |
| 5,276,138 A | 1/1994 | Yamada et al. .......... 530/357 |
| 5,306,309 A | 4/1994 | Wagner et al. ........... 623/17 |
| 5,358,935 A | * 10/1994 | Smith et al. ............. 514/21 |
| 5,390,683 A | 2/1995 | Pisharodi ............... 128/898 |

(List continued on next page.)

FOREIGN PATENT DOCUMENTS

| | | |
|---|---|---|
| CN | 1056986 A | 12/1991 |
| DE | 531446 | 1/1941 |
| DE | 3922203 C1 | 10/1990 |
| DE | 4222763 A1 | 1/1994 |
| EP | 0454600 A | 10/1991 |
| JP | 59-155248 | 9/1984 |

OTHER PUBLICATIONS

Yamauchi, et al., "Cultivation of fibroblast cells on keratin–coated substrata," Polymers for Tissue Engineering, 329–40, 1998.

Wake, et al., "Dynamics of Fibrovascular Tissue Ingrowth in Hydrogel Foams," Cell Transplantation 4(3), 275–79, 1995.

Southwest Research Institute Annual Report, 17–18, 21, 1997.

Plant, et al., "Axonal growth within poly (2–hydroxyethyl methacrylate) sponges infiltrated with Schwann cells and implanted into the lesioned rat optic tract," Brain Research, 671, 119–30, 1995.

Technology Today, 16(3):9, 1995.

Rhodes, et al., "Characteristics of the alpha–keratose fraction of hair inducing ascosporogensis in nannizzia grubyia," Mycopathologia et Mycologia Applicata, 33, 345–48, 1967.

Chargaff, et al., "Techniques for the demonstration by chromatography of nitrogenous lipide constituents, sulfur–containing amino acids, and reducing sugars," J. Biol. Chem., 175(1):67–71, 1948.

Primary Examiner—Sabiha Qazi
Assistant Examiner—Marina Lamm
(74) Attorney, Agent, or Firm—Timothy S. Corder; Stephen J. Moloney; Vinson & Elkins L.L.P.

(57) ABSTRACT

A keratin hydrogel which can be used as a wound dressing and cell scaffolding. The keratin hydrogel is formed from clean, washed hair by partially oxidizing a significant percentage of disulfide linkages to form cysteic acid groups, while some disulfide linkages remain intact. The partially oxidized hair is treated with a reducing agent, thereby reducing most of the remaining disulfide linkages to cysteine-thioglycollate disulfide and cysteine groups. A soluble fraction of hair is collected and oxidized, such that the reduced sulfur groups are allowed to reform disulfide linkages, thereby binding the keratin together. The cysteic acid groups remain, providing hydrophilic sites within the hydrogel. A higher degree of partial oxidation results in a greater abundance of hydrophilic cysteic acid groups in the hydrogel.

4 Claims, No Drawings

U.S. PATENT DOCUMENTS

| | | | |
|---|---|---|---|
| 5,443,514 A | 8/1995 | Steffee | 623/17 |
| 5,458,643 A | 10/1995 | Oka et al. | 623/18 |
| 5,480,430 A | 1/1996 | Carlisle et al. | 623/8 |
| 5,505,732 A | 4/1996 | Michelson | 606/61 |
| 5,514,180 A | 5/1996 | Heggeness et al. | 623/17 |
| 5,522,898 A | 6/1996 | Bao | 623/17 |
| 5,534,028 A | 7/1996 | Bao et al. | 623/17 |
| 5,534,029 A | 7/1996 | Shima | 623/17 |
| 5,549,679 A | 8/1996 | Kuslich | 623/17 |
| 5,562,736 A | 10/1996 | Ray et al. | 623/17 |
| 5,645,597 A | 7/1997 | Krapiva | 623/17 |
| 5,660,857 A | 8/1997 | Haynes et al. | 424/450 |
| 5,674,295 A | 10/1997 | Ray et al. | 623/17 |
| 5,676,702 A | 10/1997 | Ratron | 623/17 |
| 5,702,455 A | 12/1997 | Saggar | 623/17 |
| 5,705,780 A | 1/1998 | Bao | 204/157.15 |
| 5,712,252 A | 1/1998 | Smith | 514/21 |
| 5,716,415 A | 2/1998 | Steffee | 623/17 |
| 5,725,582 A | 3/1998 | Bevan et al. | 623/17 |
| 5,763,583 A | 6/1998 | Arai et al. | 530/353 |
| 5,766,252 A | 6/1998 | Henry et al. | 623/17 |
| 5,792,090 A | 8/1998 | Ladin | 602/48 |
| 5,800,549 A | 9/1998 | Bao et al. | 623/17 |
| 5,824,093 A | 10/1998 | Ray et al. | 623/17 |
| 5,824,331 A | 10/1998 | Usala | 424/424 |
| 5,842,477 A * | 12/1998 | Naughton et al. | 128/898 |
| 5,854,207 A | 12/1998 | Lee et al. | 514/2 |
| 5,865,846 A | 2/1999 | Bryan et al. | 623/17 |
| 5,888,224 A | 3/1999 | Beckers et al. | 623/17 |
| 5,916,870 A | 6/1999 | Lee et al. | 514/2 |
| 5,932,552 A | 8/1999 | Blanchard et al. | 514/21 |
| 5,948,428 A | 9/1999 | Lee et al. | 424/426 |
| 5,976,186 A | 11/1999 | Bao et al. | 623/17 |
| 6,022,376 A | 2/2000 | Assell et al. | 623/17 |
| 6,066,325 A * | 5/2000 | Wallace et al. | 424/400 |
| 6,113,639 A | 9/2000 | Ray et al. | 623/11 |
| 6,124,273 A * | 9/2000 | Drohan et al. | 514/55 |

* cited by examiner

KERATIN-BASED HYDROGEL FOR BIOMEDICAL APPLICATIONS AND METHOD OF PRODUCTION

CROSS-REFERENCE TO RELATED APPLICATIONS

This application is a continuation of U.S. patent application Ser. No. 09/365,699, filed Aug. 2, 1999, issued as U.S. Pat. No. 6,159,496, which is a continuation of U.S. patent application Ser. No. 08/979,456, filed Nov. 26, 1997, issued as U.S. Pat. No. 5,932,552. The present application is related to U.S. Pat. No. 5,979,526, entitled KERATIN-BASED SHEET MATERIAL FOR BIOMEDICAL APPLICATIONS AND METHOD OF PRODUCTION. The present application is also related to U.S. Pat. No. 5,358,935, entitled NONANTIGENIC KERATINOUS PROTEIN MATERIAL, both herein incorporated by reference.

FIELD OF THE INVENTION

The present invention is related to wound dressing materials and tissue engineering scaffolds. More specifically, the present invention is related to a cross-linked keratin hydrogel.

BACKGROUND OF THE INVENTION

Chronic wounds can be caused by a variety of events, including surgery, prolonged bedrest and traumatic injuries. Partial thickness wounds can include second degree burns, abrasions, and skin graft donor sites. Healing of these wounds can be problematic, especially in cases of diabetes mellitus or chronic immune disorders. Full thickness wounds have no skin remaining, and can be the result of trauma, diabetes (e.g., leg ulcers) and venous stasis disease, which can cause full thickness ulcers of the lower extremities. Full thickness wounds tend to heal very slowly. Proper wound care technique including the use of wound dressings is extremely important to successful chronic wound management. Chronic wounds affect an estimated four million people a year, resulting in health care costs in the billions of dollars. "Treatment of Skin Ulcers with Cultivated Epidermal Allografts," T. Phillips, O. Kehinde, and H. Green, *J. Am. Acad. Dermatol.*, V. 21, pp. 191–199 (1989).

The wound healing process involves a complex series of biological interactions at the cellular level which can be grouped into three phases: hemostasis and inflammation; granulation tissue formation and reepithelization; and remodeling. "Cutaneous Tissue Repair: Basic Biological Considerations," R. A. F. Clark, *J. Am. Acad. Dermatol.*, Vol. 13, pp. 701–725 (1985). Keratinocytes (epidermal cells that manufacture and contain keratin) migrate from wound edges to cover the wound. Growth factors such as transforming growth factor-$\beta$ (TGF-$\beta$) play a critical role in stimulating the migration process. The migration occurs optimally under the cover of a moist layer. Keratins have been found to be necessary for reepithelization. Specifically, keratin types K5 and K14 have been found in the lower, generating, epidermal cells, and types K1 and K10 have been found in the upper, differentiated cells. Wound Healing: Biochemical and Clinical Aspects, I. K. Cohen, R. F. Diegleman, and W. J. Lindblad, eds., W. W. Saunders Company, 1992. Keratin types K6 and K10 are believed to be present in healing wounds, but not in normal skin. Keratins are major structural proteins of all epithelial cell types and appear to play a major role in wound healing.

An optimum wound dressing would protect the injured tissue, maintain a moist environment, be water permeable, maintain microbial control, deliver healing agents to the wound site, be easy to apply, not require frequent changes and be non-toxic and non-antigenic. Although not ideal for chronic wounds, several wound dressings are currently on the market, including occlusive dressings, non-adherent dressings, absorbent dressings, and dressings in the form of sheets, foams, powders and gels. Wound Management and Dressing, S. Thomas, The Pharmaceutical Press, London, 1990.

Attempts have been made to provide improved dressings that would assist in the wound healing process using biological materials such as growth factors. To date, these biologicals have proven very costly and shown minimal clinical relevance in accelerating the chronic wound healing process. In cases of severe full thickness wounds, autografts (skin grafts from the patient's body) are often used. Although the graft is non-antigenic, it must be harvested from a donor site on the patient's body, creating an additional wound. In addition, availability of autologous tissue may not be adequate. Allografts (skin grafts from donors other than the patient) are also used when donor sites are not an option. Allografts essentially provide a "wound dressing" that provides a moist, water permeable layer, but is rejected by the patient usually within two weeks and does not become part of the new epidermis.

What would be desirable and has not heretofore been provided is a wound dressing that protects the injured tissue, maintains a moist environment, is water permeable, is easy to apply, does not require frequent changes and is non-toxic and non-antigenic, and most important, delivers effective healing agents to the wound site.

Tissue engineering is a rapidly growing field encompassing a number of technologies aimed at replacing or restoring tissue and organ function. The consistent success of a tissue engineered implant rests on the invention of a biocompatible, mitogenic material that can successfully support cell growth and differentiation and integrate into existing tissue. Such a scaffolding material could greatly advance the state of the tissue engineering technologies and result in a wide array of tissue engineered implants containing cellular components such as osteoblasts, chondrocytes, keratinocytes, and hepatocytes to restore or replace bone, cartilage, skin, and liver tissue respectively.

SUMMARY OF THE INVENTION

The present invention includes a hydrogel formed of cross-linked keratin not requiring an added binding agent. The hydrogel is believed to be bound together by reformed disulfide linkages and hydrogen bonds. A preferred use of the hydrogel is as a wound healing agent. Another preferred use is as a tissue engineering cell scaffold for implant applications. Yet another preferred use is as a skin care product. The hydrogel can be formed from a soluble protein fraction derived from hair. Keratin can be obtained from a number of sources including human or animal hair, and finger or toe nails, with one source being hair of the patient or donors.

The hydrogel can be formed by providing clean, washed, rinsed, and dried hair. The hair is partially oxidized with an oxidizing agent such as peracetic acid. The partial oxidation cleaves some disulfide linkages while leaving others intact. The cleaved bonds can form sulfonic acid residues. The partially oxidized hair can be recovered with filtration, rinsed with deionized water, dried under vacuum, and ground to a powder.

The partially oxidized powder can then have some of the remaining intact disulfide linkages cleaved with a reducing agent such as ammonium thioglycollate in ammonium hydroxide by suspending the powder in such a reducing solution. The protein suspension can be heated to about 60° for about 4 hours and cooled to room temperature. The cleaved disulfide linkages are reduced to form cysteine groups and cysteine-thioglycollate disulfide groups, solubilizing the protein even further. The insoluble keratin fraction is preferably removed from the suspension by centrifuging the suspension and collecting the supernatant. The supernatant is preferably purified using a method such as dialysis. The supernatant can be further concentrated, in one method, by application of vacuum at ambient or sub-ambient temperatures.

The supernatant, having keratin with sulfonic acid groups, cysteine groups, and cysteine-thioglycollate disulfide groups, is now oxidized to allow formation of disulfide linkages between protein backbones. The sulfonic acid residues remain as hydrophilic sites within the protein. The hydrophilic sites bind water in the hydrogel.

The hydrogel is thus formed of pure keratin, bound together with disulfide linkages and hydrogen bonds. The hydrogel requires no binders. The keratin hydrogel provides a non-antigenic, mitogenic wound healing agent that maintains wound moisture and provides a scaffold for cell growth for tissue engineered implants. Another application for this keratin gel is as a skin care product.

Keratin has been shown to be biocompatible, non-immunogenic, not to inhibit activated T-cells and therefore not interfere with the normal cell mediated immune response, and to be mitogenic for keratinocytes, fibroblasts, and human microvascular endothelial cells. Keratin has also been shown to promote epithelialization in wound healing studies on rats and humans.

DETAILED DESCRIPTION OF THE PREFERRED EMBODIMENTS

In a method according to the present invention, hair is provided, preferably washed and unbleached. The hair is harvested from a human or animal source. The patient or a human donor is a preferred source of hair, as hair from these sources is most likely to result in a non-antigenic wound healing product, although animal hair may be acceptable for certain individuals that do not have animal product allergy problems. In one method, the hair is washed with Versa-Clean TM (Fisher Scientific, Pittsburgh, Pa.), rinsed with deionized water, and allowed to air dry.

The hair can be oxidized in peracetic acid or another suitable reagent such as $H_2O_2$. A preferable treatment utilizes from 1% to 32% peracetic acid, at a temperature between about 0° C. and 100° C. for between 0.5 and 24 hours. One method treats 30 grams of hair with 500 mL of 32% peracetic acid at 4° C. for 24 hours. This treatment with peracetic acid is believed to partially oxidize the naturally occurring disulfide linkages to produce a protein with cysteic acid ($-CH_2SO_3H$) residues, and remaining disulfide linkages.

The hair is recovered, preferably with filtration through a coarse fritted glass filter, and rinsed numerous times with deionized water until the rinse solution has a pH of 6.0 or higher. The hair can then be dried in a vacuum oven at between 20° C. and 50° C. for between 0.5 and 5 days. One method dries the hair in a vacuum oven at 40° C. for several days. The dried hair can then be pulverized and ground into a fine powder. One method of grinding the hair uses a ceramic mortar and pestle.

The keratin powder can be suspended in ammonium thioglycollate. In one method, pulverized keratin powder, derived from hair as described above, is suspended in about 3N ammonium hydroxide containing ammonium thioglycollate. About six grams of keratin powder can be added per 75 mL of ammonium hydroxide. The strength of ammonium hydroxide is preferably about 3N and the preferred concentration of ammonium thioglycollate is about 11 mL (as thioglycollic acid) per 75 mL of ammonium hydroxide. The suspension can then be heated for a time sufficient to solubilize the soluble fraction of the hair. The suspension in one method is heated between 50° and 90° C. for between 1 and 24 hours, followed by cooling. In a preferred method, the suspension is heated to about 60° C. for about 4 hours and cooled to room temperature. Applicants believe this treatment cleaves the remaining disulfide linkages to produce cysteine residues in the protein structure. At this point, the keratin protein is believed to contain cysteic acid, cysteine and cysteine-thioglycollate disulfide residues. The ratio of cysteic acid residues and cysteine residues can be controlled by varying the time, temperature, and concentration of oxidant in the peracetic acid treatment step previously described. The presence of sulfonic acid residues imparts a hydrophilic property to the hair as well as to the final hydrogel product.

After the treatment described above, a keratin fraction resistant to the treatment remains, consisting primarily of Beta keratin. This fraction is insoluble in the suspension and is removed in one method by centrifugation at about 10,000 g for about 10 minutes. The insoluble fraction is set aside for other use. A thick, jelly-like supernatant remains which includes a soluble keratin fraction. The supernatant is collected.

The supernatant is preferably purified, using a method such as dialysis. A preferred method uses dialysis against running water using a dialysis membrane (Spectra/Por TM) having a cutoff of about 8000 MW. The resulting solution is preferably concentrated to a concentration of about 0.1 grams per mL.

The keratin in solution is now ready for cross-linking to form a hydrogel. In a preferred method, an oxidizing agent is added to the keratin to crosslink the keratin proteins. Preferred oxidizing agents include hydrogen peroxide, organic peracids, peroxy carbonates, ammonium sulfate peroxide, benzoyl peroxide, and perborates. Hydrogen peroxide is preferably added to the keratin solution at about 0.5% to about 1.0% w/v, mixed well, and allowed to stand at room temperature for several days. A preferred standing time is about 3 days. The freely flowing solution slowly thickens and converts to a cross-linked hydrogel after about 72 hours.

The soluble keratin fraction from hair is thus partially oxidized so as to have the protein backbones interconnected with disulfide linkages and having sulfonic acid residues. The partially oxidized keratin is treated with a reducing agent to cleave some or all of the remaining disulfide bonds, forming thiol groups and cysteine-thioglycollate disulfide groups and solubilizing more of the keratin proteins. After removing the insoluble fraction, the keratin is oxidized to allow the formation of disulfide cross-links. Disulfide cross-links are thus reformed. As used herein, the term "reformed" refers to cross-links broken and formed later in time, where individual linkages later formed could be, but are not necessarily, between the same amino acid cysteine pairs.

A cross-linked, pure keratin hydrogel results. The hydrogel has sulfonic acid groups which are hydrophilic and bind water within the hydrogel. The number of sulfonic acid groups corresponds to the degree of keratin oxidation in the partial oxidation step.

Applicants believe the keratin product made according to this method is suitable for use as a wound healing agent and as a mitogenic cell growth scaffold for tissue engineering applications and as a nutrient support for cell growth. It is also suitable for skin care applications. Anti-bacterial additives, ointments and biologicals such as growth factors or collagen can be added to the keratin hydrogel.

EXPERIMENTAL RESULTS

A keratin-based hydrogel wound healing agent not requiring binder material was prepared from keratin derived from human hair. Human hair was obtained from males aged 12 to 20 years, washed with Versa-Clean TM (Fisher Scientific, Pittsburgh, Pa.), rinsed with deionized water and allowed to air dry. This hair was subsequently chopped into approximately 0.25 inch to 2 inch lengths using shears. Thirty grams of this hair was treated with 500 mL of 32% peracetic acid (Aldrich Chemical, Milwaukee, Wis.) at 4° C. for 24 hours. This treatment partially oxidized the disulfide linkages. The hair was recovered by filtration through a coarse fritted glass filter and rinsed numerous times with deionized water until the rinse solution was pH 6.0 or higher. The hair was dried under vacuum at 40° C. for several days until completely dry and ground to a fine powder with a ceramic mortar and pestle. The resulting material, 19 grams, was used to produce a keratin hydrogel.

Six grams of the pulverized, oxidized hair was suspended in 75 mL of 3N ammonium hydroxide containing 11 mL of ammonium thioglycollate (as thioglycollic acid). The suspension was heated to 60° C. for 4 hours and then cooled to room temperature. This treatment cleaved any remaining disulfide linkages to produce cysteine and cysteine-thioglycollate disulfide residues in the protein structure. An insoluble fraction remained which was resistant to solubilization by the ammonium hydroxide and ammonium thioglycollate. The insoluble fraction, believed to be comprised mostly of Beta-keratin, was isolated by centrifugation at 10,000 g for 10 minutes. A thick, jelly-like supernatant was removed from the centrifuged material, with the insoluble material set aside for use in a related product.

The supernatant was dialyzed for 72 hours against running water using a dialysis membrane with an 8000 MW cutoff (Spectra/Por TM). The resulting solution was concentrated to 50 mL, in-vacuo at sub-ambient temperature. The solution was treated with 3% hydrogen peroxide added at a rate of 0.5% to 1.0% w/v mixed well and allowed to stand at room temperature for 3 days. The freely flowing solution slowly thickened and converted to a crosslinked hydrogel after 72 hours. The hydrogel can be used as a wound healing agent or a cell scaffold.

The use of keratin-containing materials in promoting wound healing was demonstrated in several experiments. In a first experiment, processed human hair was incubated with cell culture media. The media/hair mixture was passed through a micro filter. Cell lines relevant to wound healing, including human microvascular endothelial cells, keratinocytes and fibroblasts, were placed in culture using this media extract. Significant proliferation of these wound healing cells was measured. Keratinocytes proliferated profusely, fibroblasts proliferated modestly, and endothelial cells proliferated profusely.

The mitogenic activity observed in fibroblast, keratinocyte, and endothelial cell cultures is additional evidence that the keratinous protein material is not only biocompatible but also mitogenic with these cell lines. Additional biocompatibility was observed when keratin microfibrils were observed microscopically to be in direct contact with cells in the cell cultures. Specifically, keratinocytes and fibroblasts were observed to adhere to and congregate around microfibrils indicating that desirous cell activity can be sustained on this naturally derived biopolymer matrix.

In a second experiment, processed human hair powder was incubated with cell culture media. The media/keratin mixture was passed through a micro filter. This media extract was used in proliferation studies with lymphocytes. The lymphocyte cell line did not proliferate, indicating the material to be non-immunogenic.

In a third experiment, processed human hair powder was incubated with cell culture media. The media/hair mixture was then passed through a micro filter. This media extract was used in proliferation studies with activated T-lymphocytes. The T-lymphocytes proliferated normally, indicating no inhibition of the normal cell-mediated immune response by the keratin. This demonstrated no inhibition of this very important function of immune cells.

In a fourth experiment, human hair was chemically treated. This produced a keratin slurry that was then cast into a sheet and chemically crosslinked to produce a nonsoluble sheet of keratin. Segments of the sheeting were then incubated with keratinocytes, fibroblasts and human microvascular endothelial cells. These cells were shown to grow and proliferate favorably on the keratin sheet. This indicates that skin component cells proliferate favorably in the presence of keratin sheeting produced by the above described method.

In a fifth experiment, twenty-eight hairless rats were wounded on either side of the dorsal midline with a dermatome, creating a partial thickness wound, 0.12 inches in depth, and 2.0×4.0 cm in surface area. Half the wounds were treated with keratin powder, half were not, and both halves were covered with polyurethane dressing. The wounds were observed for healing and biopsied at days 0, 2, 4 and 6 for histochemical analysis. Planimetry studies showed 97% epithelialization of the keratin treated wounds and 78% epithelialization of the non-treated wounds at day 4. Histological analysis by H & E stain revealed total epithelialization microscopically of the keratin treated wounds at day 2 and only partial epithelialization of the non-treated wounds at day 2. Histological analyses at days 4 and 6 also revealed an acceleration of the epithelialization maturation process in the keratin treated wounds.

Human clinical studies are currently being performed on donor sites for skin grafts. One half of the donor wound site is treated with sterilized keratin powder and the opposite half treated in a standard fashion, with Adaptic TM nonadhering dressing from Johnson & Johnson. Preliminary results show the keratin treated halves epithelialize sooner and mature more rapidly. This was confirmed through both clinical observations and histological results of 4 millimeter punch biopsies. Subjectively, patients also have much less pain in the keratin treated wounds.

Numerous characteristics and advantages of the invention covered by this document have been set forth in the foregoing description. It will be understood, however, that this disclosure is, in many respects, only illustrative. Changes may be made in details, particularly in matters of shape, size, and ordering of steps without exceeding the scope of the invention. The invention's scope is, of course, defined in the language in which the appended claims are expressed.

What is claimed is:

1. A method of engineering tissue comprising the implantation of a tissue engineering scaffold comprising a keratin hydrogel comprising reformed keratin-to-keratin disulfide links.

2. The method of claim 1, wherein said keratin hydrogel is derived primarily from human hair.

3. The method of claim 1, wherein said keratin includes keratin bound together with covalent, disulfide links, and said keratin has ionic groups responsible for the hydrophilic property.

4. The method of claim 1, wherein said hydrogel has a concentration in the range of 0.05 to 0.4 grams of keratin per mL.

* * * * *